United States Patent [19]
Gutierrez

[11] 4,014,344
[45] Mar. 29, 1977

[54] DECOMPRESSION BEDS FOR CHILDBIRTH AND METHOD FOR USING THEM

[76] Inventor: Moises Hernandez Gutierrez, Avenida de las Americas 932, Guadalajara, Jalisco, Mexico

[22] Filed: Dec. 16, 1975

[21] Appl. No.: 641,357

Related U.S. Application Data

[63] Continuation-in-part of Ser. No. 404,910, Jan. 11, 1973, abandoned, which is a continuation-in-part of Ser. No. 322,720, Oct. 10, 1973, abandoned.

[52] U.S. Cl. .................................... 128/361; 5/68; 128/298
[51] Int. Cl.² ................. A61B 17/42; A61G 07/06
[58] Field of Search ....... 128/361, 303 R, 297–299; 5/68

[56] References Cited

UNITED STATES PATENTS

| | | | |
|---|---|---|---|
| 2,582,565 | 1/1952 | Schnippel et al. | 5/68 X |
| 3,062,215 | 11/1962 | Heyns | 128/361 |
| 3,742,527 | 7/1973 | Johnson et al. | 5/68 |
| 3,839,753 | 10/1974 | Benoit et al. | 5/68 |

FOREIGN PATENTS OR APPLICATIONS 1,172,987 12/1969 United Kingdom ............... 128/361

OTHER PUBLICATIONS

Scott et al. – Lancet – pp. 1181–1183, May 28, 1960.

*Primary Examiner*—Dalton L. Truluck
*Attorney, Agent, or Firm*—Fleit & Jacobson

[57] ABSTRACT

A decompression system including a hydraulically operated bed. The bed comprises head and foot elements which pivot about axes transverse to the length of the bed for comfort of the expectant patient, and a frame which tilts 15° right and left about an axis parallel to the length of the bed for shifting the position of a fetus. The bed is provided with a decompression chamber, as well as electronic monitoring equipment. Also disclosed is the method for utilizing a tilting bed while developing a vacuum acting on the patient to relieve contraction pains and to facilitate childbirth.

8 Claims, 9 Drawing Figures

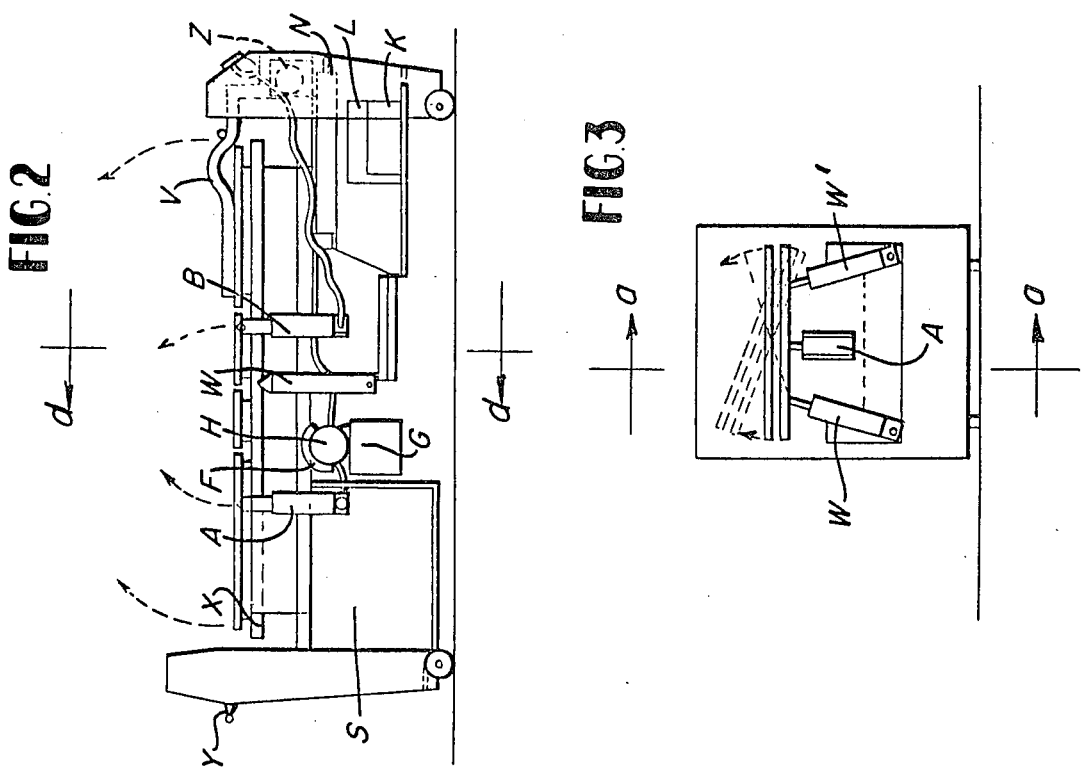
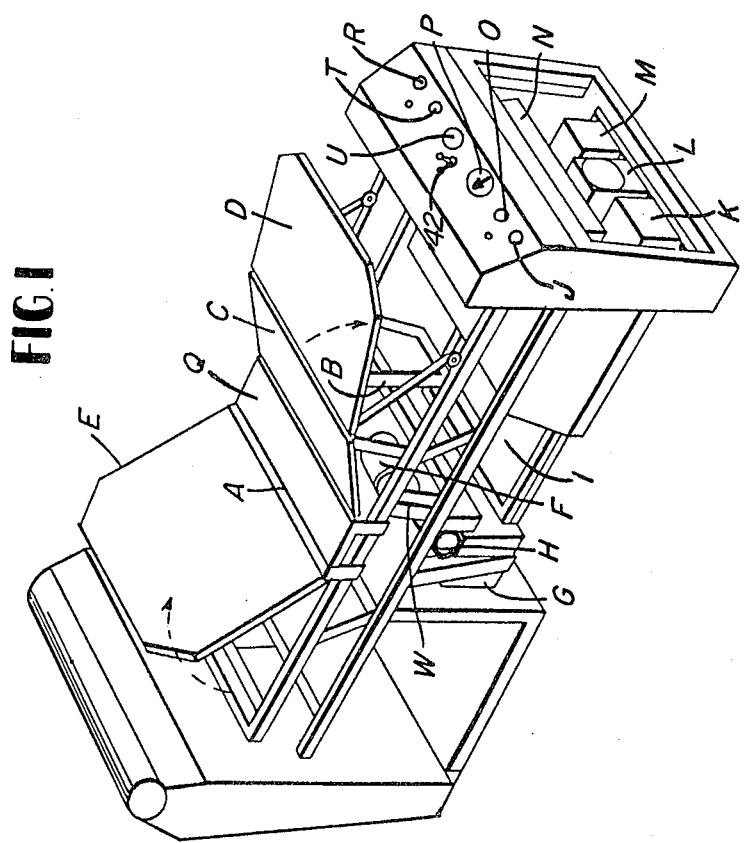

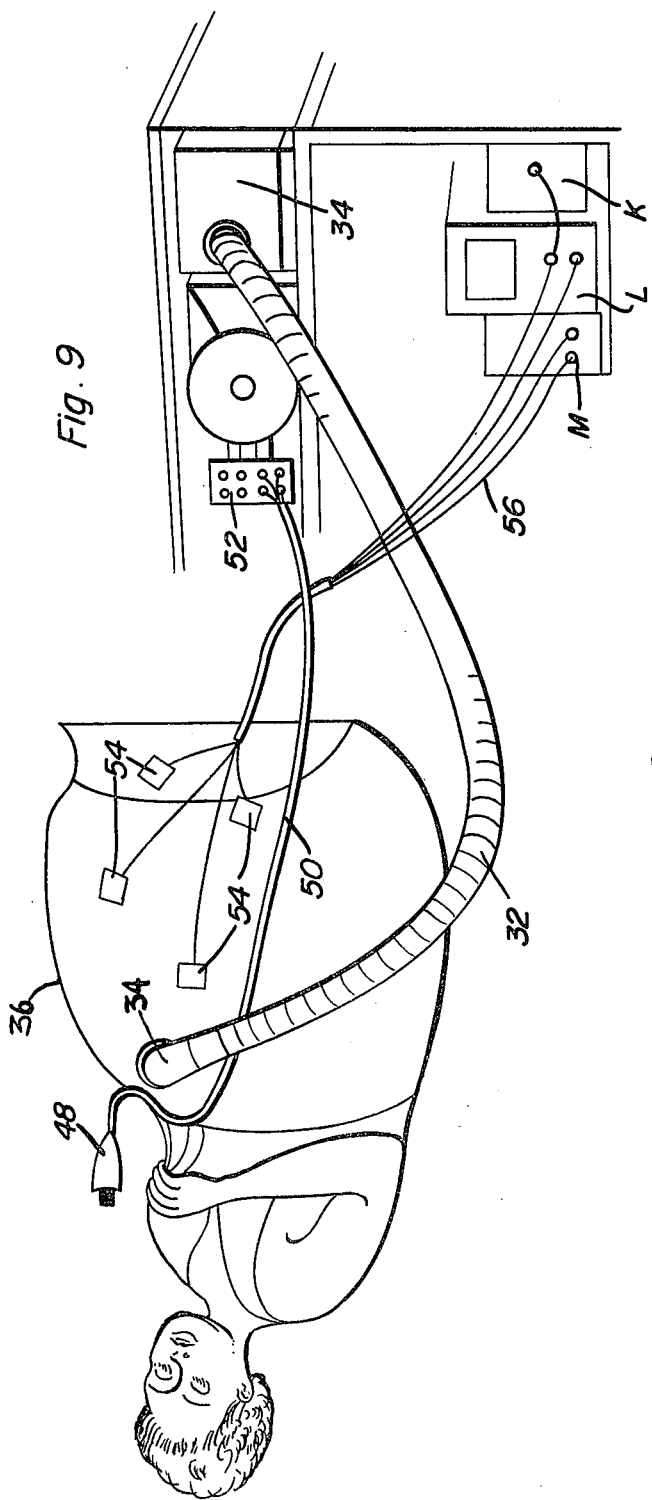
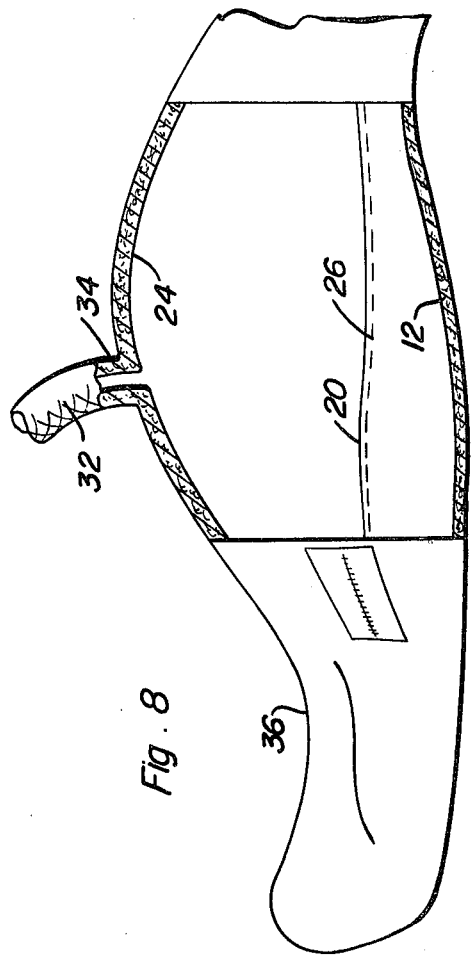

DECOMPRESSION BEDS FOR CHILDBIRTH AND METHOD FOR USING THEM

REFERENCE TO RELATED APPLICATION

This is a continuation-in-part of U.S. Pat. application Ser. No. 404,910, filed 01/11/73, which in turn, is a continuation-in-part of U.S. Pat. application Ser. No. 322,720, filed Oct. 10, 1973, each now abandoned.

BACKGROUND AND SUMMARY OF THE INVENTION

The present invention relates to an improved bed for childbirth in its first stage, designed to obtain a unit that solves some of the problems in the practice of obstetrics. With the inventive bed, the patient's comfort is enchanced by changing position by means of a silent hydraulic system. A 15° grade change of right and left positions of the bed makes the fetus rotation easier when it has a right and left in-uterus back position. The patient is made more comfortable by utilizing a decompression system during the first stage of childbearing. The inventive system also includes monitoring equipment, including that for taking a fetal electrocardiogram, for timely diagnosis of pain and fetus condition during childbearing.

The inventive device includes three basic elements, a tilting bed, a decompression chamber and electronic sensing equipment. The hydraulic bed tilts 15° right and left to change the position of the mother towards the opposite fetal side, in-uterine position, to rotate the fetal presentation of occipito-sacral to occipito anterior. The decompression chamber is used for the first childbirth period, and eases maternal-placenta-fetal blood interchange and consequently results in a greater contribution of oxygen. The chamber also reduces the contractile uterine pain and acts directly over the cervical dilatation, shortening the times of labor. The electronic unit includes phonomonitorization and electrocardiography to detect the fetal cardiocirculatory conditions during the first stage of labor.

The 15° tilting, or inclination of the bed relative to its longitudinal axis facilitates the fetal rotation presentations in the uterine positions. The occipito-sacral presentations or oblique retained, are considered as problem positions, because of their difficult rotation in most of the cases, making the labor longer and most exhausting for the mother.

If a child maintains a right occipito-sacral presentation, the 15° inclination will be to the opposite side, towards the left, facilitating rotation of the presentation towards the anterior plane. The contary happens in the left occipito-sacral presentation, since the 15° inclination will be to the right, resulting in the same effects of rotation in the presentation, assisted by the change of weight of the fetal position inside the uterus. With the assistance of the inventive bed and the changes in inclination in its movements, there have resulted reductions in labor, thus eliminating suffering and trauma in the mother and child.

The inventive obstetrical apparatus contains as a part of the unit, a complete vacuum system to develop a decompression ambient inside a capsule used in the first stage of labor.

The vacuum system comprises three basic elements. The first is a seat preferably of fiber glass, generally conforming to the body of the mother. The second element may be termed a capsule also of fiber glass, and adapted to mate with the seat. The third element is a bag made out of a strong plastic covering the body of the patient from the inferior extremities, abdomen, thorax, up to the armpits and chest. The bag is equipped with a plastic zipper, and with the seat and capsule, forms an hermetically closed chamber to establish a vacuum inside. The bag has a window, placed to the right lateral side, also having a plastic zipper for checking the conditions of the uterus neck and its expansibility as well as for diagnosing fetal positions. The presence of a window in the bag enables examination without the need for disconnecting the decompression equipment.

The electronic system forming a part of the inventive obstetrical unit offers the advantages of enabling the continuous sensing of the fetal cardiocirculating conditions during labor, and hence the continuous evaluation of these conditions, both in the hospital area and by telephonic remote control.

The audible frequency, rhythm, intensity and sound of the heartbeat is sensed during labor in the first stage. Also monitored is an image over a screen, revealing the graphical characteristics of the cardiac conditions of the fetus and the changes which occur in the childbirth process. A printed fetal electrocardiogram is also provided in the inventive decompression obstetrical unit.

It is known that the uterine contractions cause pain, and the tetanization of muscular fibres in labor diminish the maternal-fetal-placental blood circulation. Consequently the cerebral oxygenation of the fetus diminishes, producing varying degress of hypoxia, which could result in asphyxia and brain damage in the baby, depending upon the physiological characteristics of uterine contractions in intensity, frequency and duration, as well as the duration of labor up to the fetal expulsion. When uterine contraction is present, a positive pressure inside the body takes place, pressing the muscular fibres of the inferior segment of the uterus and provoking the dilatation of the uterine neck for childbirth.

When the positive pressures are transformed inside the uterus into negative ones by means of decompression by placing the mother inside a vacuum chamber, when in labor, the positive pressures are transformed to negative pressures inside the uterus. In this manner, the contraction of the muscular fibres is reduced, and the circulatory flow between mother and fetus is increased. Consequently brain oxgenation does not suffer, and instead increases due to an increase of the sanguineous flow in each uterine contraction. Futhermore, because the tetanization of uterine muscular fibres causes pain in childbirth, the abdominal and uterine expansion makes negative the pressures inside the uterus by means of the vacuum so that the pain symptom disappears. In addition, decompression reduces the time of labor.

Decompression speeds the cervical dilatation and hence shortens the time of labor. The mechanism through which this is obtained is based on the fact that during spontaneous labor, the positive pressures produced by uterine contraction over the presentation act directly over the internal opening of uterus. With the use of decompression, positive pressures are transformed into negative pressures. In this manner, the muscular contracting force is weaker, and is inverted in direction in such a manner that the sliding of the cervical muscular fibres over the presentation is in an ascending sense.

The characteristic details of the inventive bed and decompression apparatus and described and clearly shown in the following description and accompanying drawings. The same reference numbers indicate the same parts shown in the drawings.

BRIEF DESCRIPTION OF THE DRAWINGS

FIG. 1 is a perspective view of the decompression bed;

FIG. 2 is a side view of the bed illustrated in FIG. 1;

FIG. 3 is a plan view of the unit illustrated in FIG. 1, showing the hydraulic system of the decompression bed;

FIG. 8 is a schematic drawing, partially in cross section, illustrating the plastic bag utilized in developing a vacuum; and FIG. 9 is a schematic perspective illustrating the association between the patient and the elements of the inventive bed.

DETAILED DESCRIPTION OF THE DRAWINGS

Figure 4:
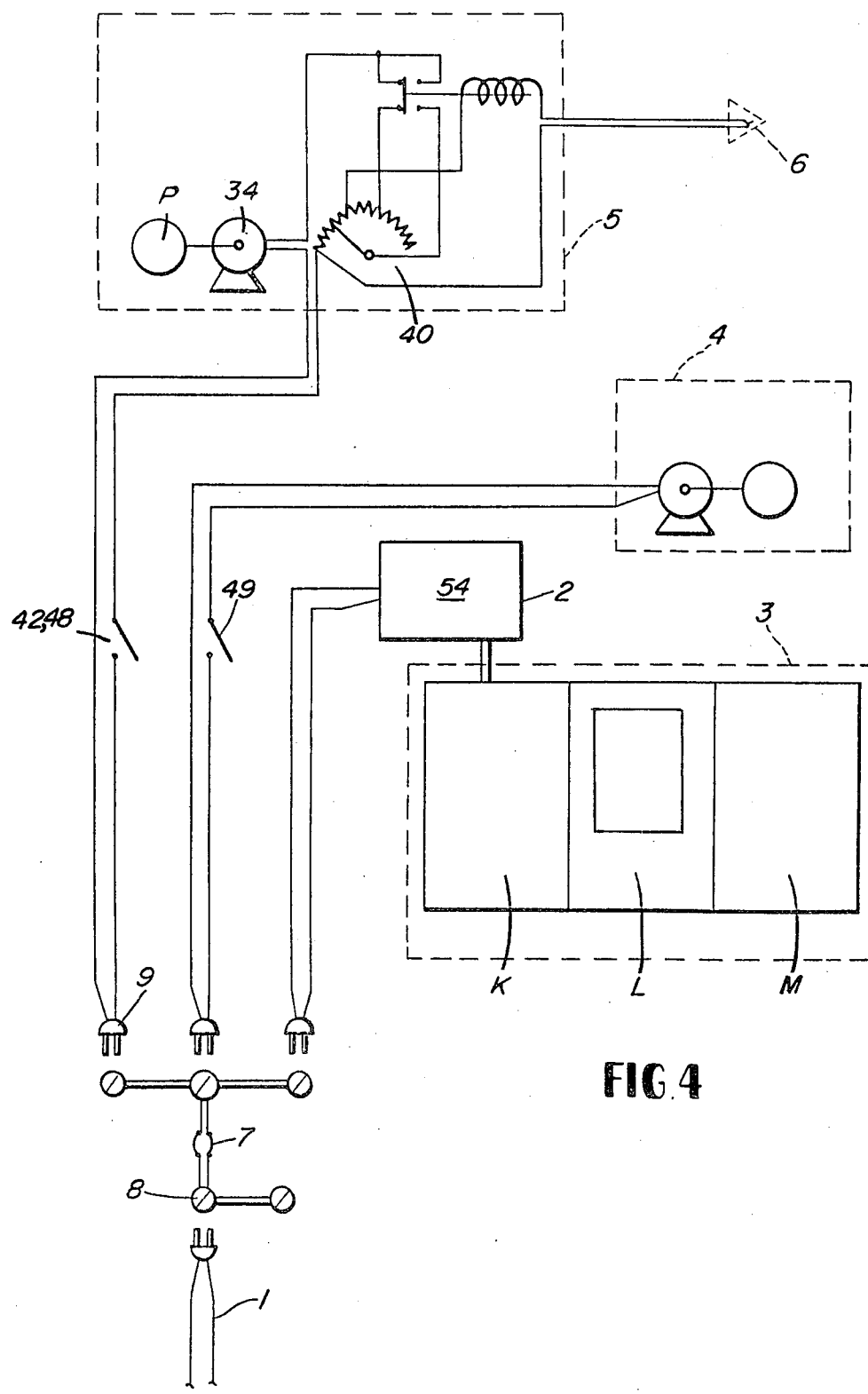
FIG. 4 is a general view of the electrical circuit by which the bed operates.

With reference first to FIGS. 1 through 3, the structure of the inventive bed will be described, as will the capability of the bed to change the position of the patient and fetus.

The inventive bed is equipped with a 1750 R.P.M. motor F which provides the power for a hydraulic cylinder H. Cylinder H, in turn, moves several pistons and is associated with an oil reservoir G. Four pistons W, W', A and B are shown in the drawings, and each produces a different effect on the position of the bed. These positions are illustrated in FIGS. 1, 2 and 3, and are controlled from a panel switchboard at the foot of the bed, including controls J, O, T and R. Switch J actuates piston A and moves the head of the bed or the spring frame up or down about an axis transverse to the length of the bed in order to position the patient's upper body. Switch R actuates piston B which similarly associates with the foot of the bed to position the lower body of the patient about an axis transverse to the length of the bed. Control O actuates piston W and orients the bed about an axis parallel to the length of the bed in order to effect a 15° grade right side inclination. Similarly, control T actuates piston W' to effect a 15° grade left side inclination. FIG. 1 shows the head and foot of the bed in their respective upper positions, and FIG. 3 illustrates, in phantom, the inclinations about a major axis of the bed.

The control panel is also equipped with a manometer P which indicates the grade of decompression experienced, or set by regulator U.

As best seen in FIGS. 1 and 2, the bed is equipped with a four-element support. The patient lies on thigh and foot panels C and D, respectively, and head panel E. These panels are pivotally mounted on the bed frame and associate with fixed panel Q. The inventive bed also includes a shelf, or storage bin S, a handle Y for moving the bed, a frame support X, and a device V for additional movement, or adjustment of leg position. The control panel at the foot of the bed is also provided with an electrocardiograph apparatus K, a fetal monitor L, including a phono monitor M and a shelf N.

The basic operation of the inventive decompression bed is as follows wherein bed movement is controlled by circuit 4 (FIG. 4) through panel switch 49. The vertical position of the bed head is adjusted to give comfort to the patient, and to best adjust the position of the decompression capsule (which will be described in detail below). The plastic bag of the decompression chamber is then closed, and completes the space formed with the patient's body. Then, the patient and the decompression equipment are placed in a horizontal orientation, the position most comfortable for the patient during the early stages of childbirth.

The panels at the bed foot are adjusted to facilitate flection of the patient's legs, and so that the patient is kept comfortable during the early stages of childbearing. This adjustment also facilitates arterio-venous circulation of the legs.

The capability of the inventive bed to produce right and left side inclinations is important in situations such as, for example, when there is a rotation of the fetus position in in the womb. This inclination feature is also of importance when the gynecologist considers that the right and left occipito-sacral positions present pathological problems that cause pain and extend the process of childbirth, thus causing the great problems and obstetric trauma frequently found in children. Experience has taught that if the mother's position is changed to the opposite fetal in-uterus position, fetus rotation is facilitated. Therefore, by use of the inventive bed, the labor time is physiologically shortened.

Figure 5:
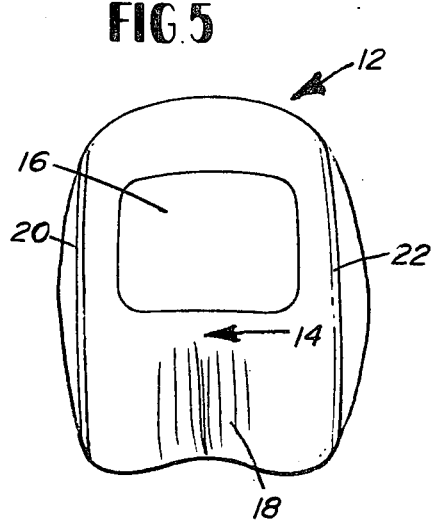
FIG. 5 is a view of the base of the decompression chamber, in the form of a seat on which the patient lies during the early stages of childbirth.

The decompression equipment, as illustrated in FIGS. 5 through 9, operates in combination with the inclination feature of the inventive bed to facilitate childbirth and increase the comfort of the mother, and takes the form as described herein. A fiberglass capsule is formed by two associating parts. One part, illustrated in FIG. 5, is a back 12 with a seat portion, shown generally at 14. Back 12 is made out of fiberglass, and includes a back window 16 for the comfort of the patient. The back 12 has a concave form, and is designed for comfort of the musculature of the gluteous region. A region 18 is curved to conform with the legs.

Laterally, back 12 has a channel in each side for mating with the cover (FIG. 6) to define an integral form for the bag. The respective channels are illustrated at 20 and 22.

Figure 6:
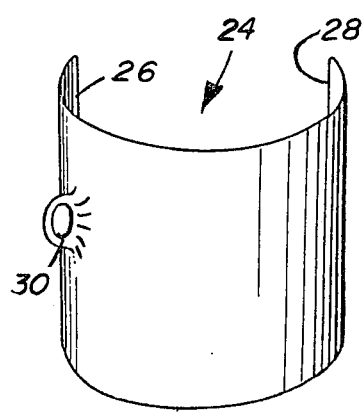
FIG. 6 is a view of a cover, or capsule, which mates with the base shown in FIG. 5 during decompression.
Figure 7:
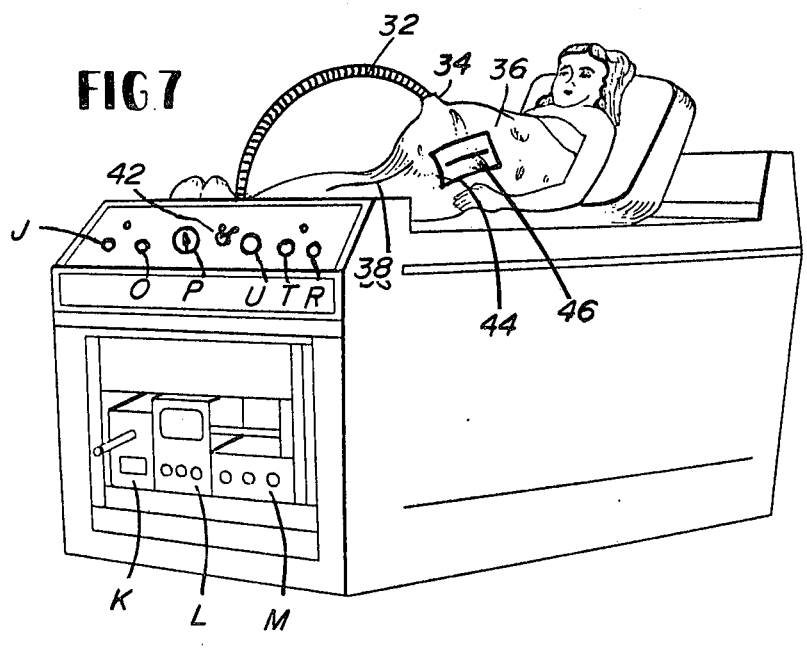
FIG. 7 is a generalized perspective view of a patient on the bed of FIG. 1, and as associating with the decompression mechanism.

The cover, or capsule of the decompression unit is shown at 24 in FIG. 6. The capsule is of strong fiberglass to thereby resist substantial pressures. The capsule 24 is placed over the back 12, with the lateral edges 26 and 28 of capsule 24 inside the respective lateral channels 20 and 22 of the base. In the upper part of the capsule 24, is a hole 30 of approximately 1½ inches in diameter. A hose 32 (FIG. 7) with a diameter of aproximately 1½ inches is connected at hole 30 by means of an hermetic plug 34. The hose 32 is connected to an aspiration pump 34 in the rear portion of the bed foot.

A strong plastic bag 36 covers the base 12 and the capsule 24, and enables obtaining a vacuum inside the decompression chamber which covers the thorax and womb. As further illustrated in FIGS. 7 and 8, the plastic bag of the inventive unit also includes a zipper 38, which may also be of a plastic material. The bag 36, capsule 24 and seat 12 form a closed chamber completely covering the patient's legs and body, up to the armpits, thus hermetically closing the circuit. In the vacuum circuit 5 (FIG. 4), the aspiration pump 34 develops the desired vacuum in the decompression through the means of an electric motor 34 whose negative pressures are recorded by the manometer (P). A rheostat 40, operating through a relay 6 controls the vacuum speed in all its variations as set by regulator (U). This decompression system is controlled by a micro-switch 42 operated at the switchboard at the foot of the bed and the hand held switch 48.

The bag 36 has a window 44 placed to the right lateral side, with a plastic zipper 46 which is desirable for constantly checking the conditions of uterus neck and its expansibility, as well as for diagnosing positions of the fetus. One of the major advantages brought about by window 44 is that when checking the mother or fetus, there is no need for disconnecting any of the decompression elements during labor, and hence there is no interruption of relief during examination practiced between contractions. The bag 36 and its rigid capsule 24 and seat 12 are designed to associate with the bed so that the weight of the expectant mother and the seat design enable the 15° left and right inclinations without displacement of the expectant mother relative to the bed surface.

For manually operating the decompression system, a switch 48 (FIGS. 4 and 9) with a cable 50 is inserted in the electrical circuit of the pump, connected in the posterior region of the command panel, as shown at 52. This switch 48 is comfortably managed by the physician, the patient or by the assisting nurse, when contractions are present.

As noted above, the inventive obstetrical unit comprises electronic apparatus at the foot of the bed. This electronic apparatus offers the advantages of an absolute control and monitoring of the fetal cardiocirculatory conditions during the accouchment labor enabling interpretation and diagnosis both in the hospital area and by telephonic remote control. The apparatus includes an audible fetal monitoring unit, a scope for displaying the graphical characteristics of the cardiac conditions of the fetus, and a device for providing a written ECG fetus tracing.

The monitoring elements are connected by means of known surface mounted sensing devices, associated in the region of the mother's womb, and shown in FIG. 9 at 54. Cables 56 connect the surface sensors 54 with input terminals at the rear of monitors (K), (L) and (M). Also see FIG. 4 where the monitoring circuit is shown at 3.

The inventive decompression system results in the following advantages. By the inventive procedure, the positive pressures of the patient's uteral contractions are converted to negative pressures by the application of the vacuum. In this manner, the maternal-fetal circulatory stream is increased, as is the oxygen received by the child in each uterine contraction during the early stages of childbirth. With the present invention, wherein positive pressures are converted into negative pressures by the development of a vacuum and the expansion of the abdominal, perineal, diaphragmatic and uterine muscular fibers, there results a reduction or complete elimination of the pain caused by the contractions of the uterus. This helps the mother, since the negative vacuum pressure is graduated in accordance with the threshold of pain, after considering the intensity, frequency and duration of each uterine contraction. Another benefit for the mother and child when using the inventive decompression apparatus is that the stretching and relaxation of the muscular fibers of the uterus neck during the early stages of childbirth is easier and faster, and therefore childbirth is accomplished in a shortened time.

The use of decompression in prenatal care is also applied as an effective treatment for toxemia of pregnancy. It can also be used to relieve monthly menstrual pains. Furthermore, the problems that frequently accompany pregnancy, like lumbago, circulatory and varicose problems, and toxemias in pregnancy (edema in the legs, disturbances in the arterial pressures, obesity, urine retention, albumin presence) also find their treatment in the inventive decompression chamber.

The decompression chamber consists of a strong plastic suit and a fiberglass dome, both airtight, to allow for the removal of air by way of a suction pump. The air pressure in the chamber is shown by a manometer.

In the normal physiology of labor before childbirth, the uterus contracts rhythmically producing pain in each contraction. Because of this, mother-fetus circulation diminishes and consequently the cerebral oxygenation of the child suffers grades of hypoxias. This is all attributable to the different positive pressures in the uterine cavity.

However, with decompression in labor, positive pressures are transformed into negative pressures, thereby changing the shape of the uterus to a more rounded form. As a consequence of practicing the present invention, there results the observable advantages of (1) greater volume of the uterine cavity, (2) greater maternal-placental-fetal circulatory contribution, and (3) increased oxygen levels in the blood passing in the umbilical cord. Furthermore, while usually undergoing contractile pain in labor, the present invention provides for stretching of the abdominal muscular fibres, thereby allowing uterine distention and thus helping pain disappear.

Likewise, the inventive decompression chamber finds use in the delivery room. The pressure in the uterus (intra-amniotic) is significantly reduced in the moment of uterine contraction, without administering decompression. Normally, the pressure in the uterine cavity during labor contractions and according to the frequency and duration of them, appears between 10, 20, 30, 70, 80 and disappearance of contractile pain. By practicing the present invention, the stretching in the uterus muscular fibres in its inferior segment (thus obtaining a quicker opening of the orifice), significantly reduces the time involved in childbirth. Statistics show labors from 10 minutes in total duration in women who have had more than one child, up to no more than three or four hours in women undergoing their first childbearing experience. Especially impressed by the present invention were mothers who had previously borne children without the benefits of decompression. As noted above, the inventive decompression bed is also equipped with auxiliary electronics for monitoring the fetus. These auxiliary devices serve to hear the fetal heart's palpitations, to obtain electrocardiograms and to monitor the same heart. This equipment is placed in a special zone of the bed, and can be easily handled in the same unit during childbirth. These devices have proved very useful because, through them, the fetus condition, pain, etc. are immediately detected.

The present invention relates generally to a bed used during the early stages of childbirth. The bed is uniquely equipped with a mechanism for tilting the surface of the bed, and hence its occupant, on the order of 15° in both directions about the major central axis of the bed. In this manner, the uterine position of the fetus can be shifted for purposes of safety to the fetus, comfort of the mother, or both. Coupled with this characteristic of the inventive bed is a decompression unit. By means of the decompression unit, after the bed has been tilted to the degree most advantageous to the mother and child, the normally positive uterine pressures are converted to negative pressures. Therefore, the safety of the fetus, the comfort of the mother, and the rapidity of the childbearing experience are all maximized. It should be understood that the invention has been described for purposes of illustration only, without intent to limit the scope of the invention in any manner whatsoever.

Thus having described my invention, I claim as my property the contents of the following:

1. An obstetric apparatus including an elongated bed for use by an expectant mother, the bed comprising: a frame element; a bed surface movably mounted on said frame element and comprising a head section and a foot section; first power means for pivotally raising and lowering said head section about a first axis transverse to the major length axis of the bed; second power means for pivotally raising and lowering said foot section about a second axis parallel to but spaced from said first axis; third power means for pivotally moving said frame element, with said head and foot sections, about a central third axis parallel to the major length axis of the bed for producing up to an approximately 15° right side inclination and up to an approximately 15° left side inclination; and vacuum means integral with and mounted on said bed, for developing a vacuum about the lower body of the expectant mother after said frame element has been pivotally moved about said third axis to maximize the safety of the fetus and the comfort of the mother, said vacuum means including means for developing a vacuum in said vacuum-tight chamber according to a predetermined rhythm coinciding with the rhythm of uterine muscular contractions experienced by the expectant mother for decompressing the expectant mother.

2. The bed recited in claim 1, wherein all of said power means are hydraulic.

3. The bed recited in claim 1, wherein said means for developing a vacuum comprises: a vacuum chamber base adapted to lie on said bed surface; a capsule for mounting on said base to form with said base, a generally open ended barrel frame about the lower body of the expectant mother, said capsule being equipped with a vacuum inlet and; a gas-tight bag for encasing said base, said capsule and the lower body of the expectant mother to form a vacuum-tight chamber therearound.

4. The bed recited in claim 1, and further comprising: means for monitoring the palpitations of the fetal heart; and means for monitoring and recording the electrical activities of such heart.

5. The bed recited in claim 1, and further comprising electronic monitoring equipment mounted on said bed and serving to monitor the condition of the fetus so as to enable adjustment of the bed frame about said third axis or the vacuum developed in said vacuum-tight chamber.

6. The bed recited in claim 1, and further comprising switch means for being operated by the expectant mother to actuate said vacuum means for relieving pain.

7. The bed recited in claim 1, and further comprising regulator means for adjusting the magnitude of the vacuum developed by said vacuum means.

8. A method for relieving an expectant mother during the early stages of childbirth, the method comprising the steps of: having the expectant mother recline on the surface of an elongated bed; tilting the surface of said bed about a central axis parallel to the major length axis of the bed up to approximately 15° left or right side inclination for maximizing the safety of the fetus and the comfort of the expectant mother; encasing the lower portion of the expectant mother's body with a vacuum-tight chamber; and developing a rhythmic vacuum in said vacuum chamber according to the rhythm of muscular contractions of the uterus.

* * * * *